United States Patent
Omura et al.

(10) Patent No.: US 9,913,788 B2
(45) Date of Patent: Mar. 13, 2018

(54) OIL-IN-WATER EMULSION COMPOSITION

(71) Applicant: SHISEIDO COMPANY, LTD., Tokyo (JP)

(72) Inventors: Takayuki Omura, Yokohama (JP); Daisuke Suzuki, Yokohama (JP)

(73) Assignee: SHISEIDO COMPANY, LTD., Tokyo (JP)

( * ) Notice: Subject to any disclaimer, the term of this patent is extended or adjusted under 35 U.S.C. 154(b) by 0 days.

(21) Appl. No.: 14/650,769

(22) PCT Filed: Jul. 1, 2013

(86) PCT No.: PCT/JP2013/004073
§ 371 (c)(1),
(2) Date: Jun. 9, 2015

(87) PCT Pub. No.: WO2013/132878
PCT Pub. Date: Sep. 12, 2013

(65) Prior Publication Data
US 2015/0328124 A1 Nov. 19, 2015

(30) Foreign Application Priority Data

Dec. 14, 2012 (JP) ................. 2012-273056

(51) Int. Cl.
| | | |
|---|---|---|
| A61K 8/73 | (2006.01) | |
| A61Q 19/00 | (2006.01) | |
| A61K 8/06 | (2006.01) | |
| A61Q 19/08 | (2006.01) | |
| A61K 8/81 | (2006.01) | |
| A61K 8/34 | (2006.01) | |
| A61K 8/37 | (2006.01) | |
| A61K 8/86 | (2006.01) | |
| A61K 8/891 | (2006.01) | |

(52) U.S. Cl.
CPC ............ *A61K 8/37* (2013.01); *A61K 8/062* (2013.01); *A61K 8/34* (2013.01); *A61K 8/345* (2013.01); *A61K 8/735* (2013.01); *A61K 8/8152* (2013.01); *A61K 8/8158* (2013.01); *A61K 8/86* (2013.01); *A61K 8/891* (2013.01); *A61Q 19/00* (2013.01); *A61Q 19/007* (2013.01); *A61Q 19/08* (2013.01); *A61K 2800/59* (2013.01)

(58) Field of Classification Search
CPC ...... A61K 8/735; A61K 8/8158; A61K 8/345; A61K 8/34; A61K 8/062; A61K 2800/59; A61Q 19/08; A61Q 19/007

USPC .......................................... 514/62
See application file for complete search history.

(56) References Cited

U.S. PATENT DOCUMENTS

| | | | |
|---|---|---|---|
| 2006/0110416 A1 | 5/2006 | Ziemkiewicz | |
| 2010/0047197 A1* | 2/2010 | Scherner | A61K 8/42 424/59 |
| 2011/0142774 A1* | 6/2011 | Tomita | A61K 8/31 424/64 |
| 2011/0213030 A1* | 9/2011 | Shinto | A61K 8/0212 514/474 |
| 2011/0236447 A1 | 9/2011 | Yoshimura | |
| 2013/0029932 A1 | 1/2013 | Sakai | |
| 2013/0122036 A1 | 5/2013 | Declercq | |

FOREIGN PATENT DOCUMENTS

| | | |
|---|---|---|
| JP | 5933 | 1/1993 |
| JP | 640886 | 2/1994 |
| JP | 7304629 A2 | 11/1995 |
| JP | 9315936 A2 | 12/1997 |
| JP | 200110946 | 1/2001 |
| JP | 200597123 | 4/2005 |
| JP | 200940705 | 2/2009 |
| JP | 200967728 | 4/2009 |
| JP | 2010229068 A2 | 10/2010 |
| JP | 201220980 | 2/2012 |
| WO | 2006056246 A1 | 6/2006 |
| WO | 2011111854 A1 | 9/2011 |
| WO | 2013006335 A2 | 1/2013 |

OTHER PUBLICATIONS

International Search Report dated Sep. 17, 2013 filed in PCT/JP2013/004073.
Matsumoto Trading Co Ltd, "Aristoflex," Oct. 1, 2007.; Cited in International Search Report.
Extended European Search Report dated Jul. 1, 2016 issued in the corresponding European patent application No. 13757986.8.

* cited by examiner

*Primary Examiner* — Yih-Horng Shiao
(74) *Attorney, Agent, or Firm* — Rankin, Hill & Clark LLP

(57) ABSTRACT

The present invention provides an oil-in-water emulsion composition that is high in the moisturizing effect and the skin smoothing effect, excellent in the improving effect on wrinkles and elasticity, good in spreadability during application, and without an oily feeling and sticky feeling.
The oil-in-water emulsion composition of the present invention is characterized by comprising the below-described components (a) hyaluronic acid or a salt thereof, (b) ammonium acryloyldimethyltaurate/beheneth-25 methacrylate crosspolymer, (c) water-holding oil, (d) glycerin, and (e) ethanol.

7 Claims, 1 Drawing Sheet

[Fig. 1]
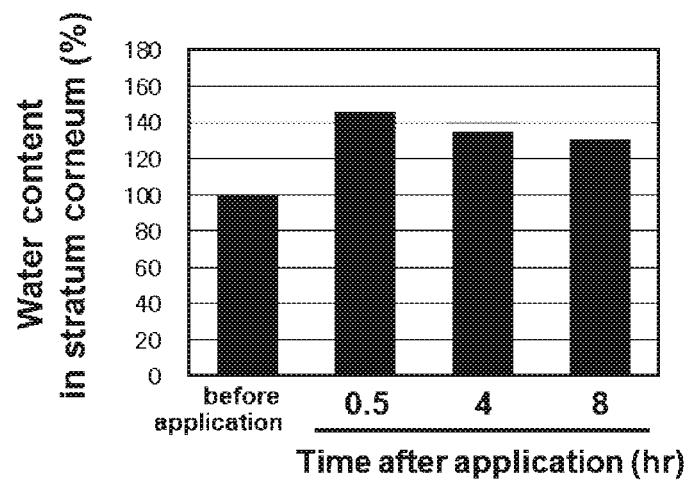
[Fig. 2]
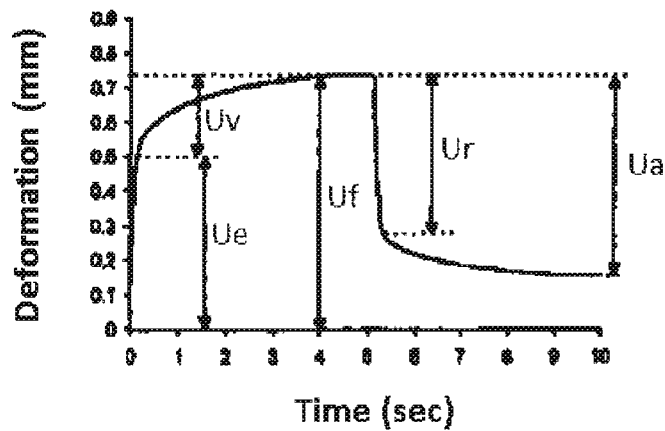

OIL-IN-WATER EMULSION COMPOSITION

TECHNICAL FIELD

The present invention relates to an oil-in-water emulsion composition.

RELATED APPLICATIONS

This application claims the priority of Japanese Patent Application No. 2012-273056 filed on Dec. 14, 2012, which are incorporated herein by reference.

BACKGROUND ART

The formation of wrinkles and the loss of an elastic feeling of the skin are the indicators of skin aging, which many women are most concerned with. Therefore, the development of cosmetics excellent in the wrinkle improving effect and the elastic feeling improving effect is much needed.

Among wrinkles, fine wrinkles at the corners of the eyes and around the mouth are considered to be caused by dry skin, and it is reported that the degree of fine wrinkles is correlated with the water content in the stratum corneum in humans (non-patent literature 1). Therefore, in many cosmetics, a wide variety of moisturizers is blended in anticipation of wrinkle preventing and wrinkle improving effects. As representative moisturizers, polyols and polyethers such as glycerin, 1,3-butylene glycol, xylitol, sorbitol, polyethylene glycol, propylene glycol, and diglycerin (ethylene oxide) (propylene oxide) adduct can be listed. However, it is difficult to obtain wrinkle preventing and wrinkle improving effects only with these compounds. In addition, there has been a problem in that a sticky feeling is generated when a large amount is blended.

Polymer compounds such as hyaluronic acid, mucoitin sulfuric acid, charonic acid, chondroitin sulfate, and soluble collagen are also used widely as the moisturizer. However, a taut feeling due to a coating feeling is easily generated, and they tend to be stickier than polyols.

On the other hand, as for the elastic feeling, improvement has been attempted thus far by blending film-forming components such as polyvinyl alcohol, sodium alginate, mucopolysaccharides and collagen, eggshell protein and degradation products thereof, and acrylic resins; spherical or other powder; crosslinked methylpolysiloxane; etc. (patent literatures 1 and 2). However, it has been known that the spreadability during application becomes poor and the sticky feeling is generated when these components are blended to the extent that the elasticity improving effect is obtained.

Thus, if the above-described moisturizers and/or film-forming components are blended in large amounts, in anticipation of the improvement of wrinkles and an elastic feeling, there have been problems in that freshness is lost, even for oil-in-water emulsion compositions, and an oily feeling and sticky feeling are generated. If a large amount of ethanol is blended to eliminate the sticky feeling, the stability of emulsion particles decreases and the irritation to the skin is generated; thus it has been difficult to blend a large amount of ethanol.

Accordingly, the preparation of cosmetics, wherein the moisturizing effect is sufficiently high, the wrinkle improving effect is recognized, the skin elasticity improving effect is excellent, the spreadability during application is good, and the oily feeling and sticky feeling are absent, has been sought-after.

CITATION LIST

Patent Literature

[PTL 1]
Japanese Unexamined Patent Application Publication No. H5-933
[PTL 2]
Japanese Unexamined Patent Application Publication No. H9-315936
[PTL 3]
Japanese Unexamined Patent Application Publication No. H6-40886
[PTL 4]
Japanese Unexamined Patent Application Publication No. 2009-67728
[PTL 5]
Japanese Unexamined Patent Application Publication No. 2012-20980

Non Patent Literature

[NPL 1]
Genji Imokawa, et al., Fragrance Journal, Vol. 11, 29-42 (1992)

SUMMARY OF INVENTION

Technical Problem

The present invention was made in view of the above-described circumstances, and an object is to provide an oil-in-water emulsion composition that is high in the moisturizing effect and skin smoothing effect, excellent in the wrinkle improving effect and elasticity improving effect, good in spreadability during application, and without an oily feeling and sticky feeling.

Solution to Problem

The present inventors have diligently studied to achieve the above-described object. As a result, the present inventors have found that ammonium acryloyldimethyltaurate/beheneth-25 methacrylate crosspolymer, which is known as a thickener, is excellent in the skin smoothing effect. It was also found that, by blending hyaluronic acid (salt) and an oil with water-holding capacity (hereinafter referred to as a water-holding oil) in addition to the polymer, an oil-in-water emulsion cosmetic without an oily feeling and sticky feeling, good in spreadability during application, excellent in the effect to make the skin moist and smooth after application, and excellent in the improving effect on wrinkles and elasticity, can be obtained even if the blending quantity of glycerin is small and the blending quantity of ethanol is large, thus leading to the completion of the present invention.

That is, an oil-in-water emulsion composition characterized by comprising (a) hyaluronic acid or a salt thereof, (b) ammonium acryloyldimethyltaurate/beheneth-25 methacrylate crosspolymer, (c) water-holding oil, (d) glycerin, and (e) ethanol can be provided by the present invention.

In the oil-in-water emulsion composition of the present invention, one or more selected from the group consisting of an alkoxysalicylic acid and a salt thereof, a 4-alkylresorcinol and a salt thereof, and a 4-alkylresorcinol derivative and a salt thereof can also be blended.

Advantageous Effects of Invention

According to the present invention, an oil-in-water emulsion composition that is very high in the moisturizing effect and the skin smoothing effect, excellent in the improving effect on wrinkles and elasticity, good in spreadability during application, and without an oily feeling and sticky feeling can be obtained. By additionally blending a whitening agent, an oil-in-water emulsion cosmetic excellent in the whitening effect, in addition to the above-described effect, can be prepared.

BRIEF DESCRIPTION OF DRAWINGS

FIG. 1 shows a time course of the water content in the stratum corneum after application of the composition of the present invention, indicating that the water retention capacity in the stratum corneum drastically increased on the treated area (arm) over a long period of time.

FIG. 2 shows a skin deformation curve and related parameters which are obtained by a measurement with the Cutometer.

DESCRIPTION OF EMBODIMENTS

Hereinafter, the preferred embodiments of the present invention will be explained. At first, the constituents of the oil-in-water emulsion composition of the present invention will be explained. POE and PEG, in the below descriptions, are abbreviations for polyoxyethylene and polyethylene glycol, and the numbers in the parentheses behind the abbreviations represent the total mole number of added POE or PEG.

(a) Hyaluronic Acid or a Salt Thereof

Hyaluronic acid usable in the present invention is not limited in particular so far as it is normally used in cosmetics. For example, hyaluronic acid isolated by the extraction from animal tissues such as cockscomb and hyaluronic acid obtained by the fermentation method with the use of microorganisms can be used. Commercial hyaluronic acids such as Biohyalo 9 (manufactured by Shiseido Co., Ltd.) or hyaluronic acid (manufactured by Kibun Food Chemifa Co., Ltd.) may be used. As hyaluronic acid salts, hyaluronic acid metal salts such as sodium hyaluronate and potassium hyaluronate can be suitably used. In addition, hyaluronic acid derivatives obtainable by the etherification, esterification, amidation, acetalization, or ketalization of the hydroxyl group, carboxyl group, etc. of hyaluronic acid may be used.

The molecular weight of hyaluronic acid or a salt thereof that is usable in the present invention is not limited in particular. The molecular weight of 100 thousands or higher is preferable, and the molecular weight of about 500 thousands to 3 millions is more preferable. The preferable blending quantity of (a) hyaluronic acid or a salt thereof in the present invention is 0.3 to 0.7 mass % in the composition.

(b) Ammonium Acryloyldimethyltaurate/Beheneth-25 Methacrylate Crosspolymer

As (b) ammonium acryloyldimethyltaurate/beheneth-25 methacrylate crosspolymer usable in the present invention, commercial products such as Aristoflex HMB (manufactured by Clariant (Japan) K.K.) can be listed.

The preferable blending quantity of (b) ammonium acryloyldimethyltaurate/beheneth-25 methacrylate crosspolymer in the present invention is 0.3 to 0.7 mass % in the composition.

(c) Water-Holding Oil

Water-holding oil used in the present invention is the oil whose percentage of water hold, which is calculated with the formula (1) after carrying out the following water-holding test, is 50% or higher.

Method for Water-Holding Test;

The initial weight of a sample (an oil component) is measured, and then the sample is heated to 70 degrees centigrade (hereinafter referred to as deg C.). While the sample is stirred, the 70 deg C.-preheated water is gradually added to the sample until water floats out on the surface of the sample. The amount of water added until the water floats out there is measured.

$$\text{Percentage of water hold} = [(\text{amount of added water (g)} + \text{initial weight of sample (g)})/\text{initial weight of sample (g)}] \times 100 \qquad \text{Formula (1)};$$

As the water-holding oil of the present invention, Softisan 649 (bis-diglyceryl polyacyladipate-2, manufactured by Sasol Ltd., percentage of water hold: 170%), pentaerythrityl tetra(behenate/benzoate/ethylhexanoate) (percentage of water hold: 50%), phytosteryl macadamiate (YOFCO-MAS, manufactured by Nippon Fine Chemical Co., Ltd., percentage of water hold: 250%), bis(phytosteryl/behenyl/isostearyl)dimer dilinoleyl dimer dilinoleate (PLANDOOL-G, manufactured by Nippon Fine Chemical Co., Ltd., percentage of water hold: 200%), etc. can be suitably used. In addition, di(phytosteryl/2-octyldodecyl)N-lauroyl-L-glutamate (Eldew PS-203, percentage of water hold: 170%), di(cholesteryl/behenyl/octyldodecyl)N-lauroyl-L-glutamate (Eldew CL-301, percentage of water hold: 120%), di(cholesteryl/octyldodecyl)N-lauroyl-L-glutamate (Eldew CL-202, percentage of water hold: 130%), di(phytosteryl/behenyl/2-octyldodecyl)N-lauroyl-L-glutamate (Eldew PS-304, percentage of water hold: 125%), di(phytosteryl/behenyl/2-octyldodecyl)N-lauroyl-L-glutamate (Eldew PS-306, percentage of water hold: 135%), isopropyl N-lauroyl sarcosinate (Eldew SL-205, percentage of water hold: 115%), phytosteryl/decyltetradecyl N-myristoyl-N-methyl beta-alaninate (Eldew APS-307, percentage of water hold: 165%), etc. can also be suitably used (all manufactured by Ajinomoto Co., Inc.). Among them, Softisan 649 is the most preferable.

The preferable blending quantity of the (c) water-holding oil of the present invention is 1.0 to 2.0 mass % in the composition.

(d) Glycerin

In the oil-in-water emulsion composition of the present invention, (d) glycerin can be blended as the moisturizer. Glycerin is the most widely used moisturizer in cosmetics, and it is known that a satisfactory moisturizing effect can be achieved by blending a large amount (normally 10 mass % or more). However, because the oil-in-water emulsion composition of the present invention has an excellent moisturizing effect, the blending quantity of glycerin can be held down to 5 mass % or less.

(e) Ethanol

In the oil-in-water emulsion composition of the present invention, (e) ethanol can be blended as a component to reduce a sticky feeling.

Generally, the blending of a large amount of ethanol is not desirable because the stability of an oil-in-water emulsion composition is impaired. In the present invention, 5 mass % or more ethanol can be blended with respect to the total composition.

In the oil-in-water emulsion composition of the present invention, other components normally used in cosmetics can be blended within the range that the effect of the present invention is not impaired. Examples of such components include emulsifiers, non-water-holding oils, moisturizers, thickeners, medicinal components, percutaneous absorption promoters, pH adjusters, antioxidants, preservatives, antimicrobial agents, neutralizers, perfume, etc.

The emulsifier is not limited in particular so far as it is normally used in cosmetics. An alkyl-modified carboxyvinyl polymer having an emulsifying power can be suitably used, and acrylates/alkyl methacrylate copolymers can be listed as an example of such polymer. Examples of commercial products of the polymer include Pemulen TR-1, Pemulen TR-2 (both manufactured by BF Goodrich Co.), etc.

Hydrophilic non-ionic surfactants can also be suitably used. POE alkyl ether type non-ionic surfactants can be listed for example, and POE(20) cetyl ether (EMALEX 120, manufactured by Nihon Emulsion Co., Ltd.), POE(25) cetyl ether (EMALEX 125, manufactured by Nihon Emulsion Co., Ltd.), POE(30) cetyl ether (EMALEX 130, manufactured by Nihon Emulsion Co., Ltd.), POE(30) behenyl ether (NIKKOL BB-30, manufactured by Nikko Chemicals Co., Ltd.,), POE(20) behenyl ether (NIKKOL BB-20, manufactured by Nikko Chemicals Co., Ltd.,), etc. are commercially available.

Among those emulsifiers, Pemulen TR-2 is the most preferable, which can be blended in the amount of 0.01 to 0.1 mass % in the composition of the present invention.

The non-water-holding oil is not limited in particular; for example, non-polar oils such as hydrocarbon oils and silicone oils, low-polarity oils such as monoester oils, etc., which are normally blended in cosmetics, can be blended.

Examples of hydrocarbon oils include olefin oligomers, liquid paraffin, ozokerite, squalane, pristane, paraffin, ceresin, squalene, petrolatum, microcrystalline wax, etc.

Examples of silicone oils include linear polysiloxanes (for example, dimethylpolysiloxane, methylphenylpolysiloxane, diphenylpolysiloxane, etc), cyclic polysiloxanes (for example, octamethylcyclotetrasiloxane, decamethylcyclopentasiloxane, dodecamethylcyclohexasiloxane, etc.), three-dimensional network silicone resin, silicone rubber, various modified polysiloxanes (amino-modified polysiloxane, polyether-modified polysiloxane, alkyl-modified polysiloxane, fluorine-modified polysiloxane, etc.), acrylic silicones, etc.

Examples of monoester oils include isopropyl myristate, cetyl octanoate, octyldodecyl myristate, isopropyl palmitate, butyl stearate, hexyl laurate, myristyl myristate, decyl oleate, hexyldecyl dimethyloctanoate, cetyl lactate, myristyl lactate, isocetyl stearate, isocetyl isostearate, etc.

Other ester oils such as pentaerythrityl tetra-2-ethylhexanoate, glyceryl tri-2-ethylhexanoate, tripropylene glycol dineopentanoate, cetyl 2-ethyhexanoate, and diethylhexyl succinate may also be used.

In the oil-in-water emulsion composition of the present invention, moisturizers other than component (d) can be blended. Examples of such moisturizers include polyethylene glycol, propylene glycol, 1,3-butylene glycol, xylitol, sorbitol, maltitol, chondroitin sulfate, mucoitin sulfuric acid, charonic acid, atelocollagen, cholesteryl 12-hydroxystearate, sodium lactate, bile salts, dl-pyrrolidone carboxylic acid salts, alkylene oxide derivatives, short-chain soluble collagen, diglycerin ethylene oxide/propylene oxide adduct, chestnut rose extract, yarrow extract, melilot extract, amino acids, nucleic acids, proteins such as elastin, mucopolysaccharides such as chondroitin sulfate, etc.

In the oil-in-water emulsion composition of the present invention, thickeners other than components (a) and (b) may be blended. Examples of such thickeners include carboxyvinyl polymer, succinoglycan, hydroxyethyl cellulose, hydroxypropyl cellulose, xanthan gum, etc.

Furthermore, in the oil-in-water emulsion composition of the present invention, various medicinal components can be blended.

For example, as the whitening agent, an alkoxysalicylic acid and/or a salt thereof (patent literature 3) can be suitably blended. Specific examples include 3-methoxysalicylic acid, 3-ethoxysalicylic acid, 4-methoxysalicylic acid, 4-ethoxysalicylic acid, 4-propoxysalicylic acid, 4-isopropoxysalicylic acid, 4-butoxysalicylic acid, 5-methoxysalicylic acid, 5-ethoxysalicylic acid, 5-propoxysalicylic acid, and salts thereof.

Also, as the whitening agent, a 4-alkylresorcinol and/or a salt thereof, or a 4-alkylresorcinol derivative and/or a salt thereof can be suitably blended. Specific examples of 4-alkylresorcinols include 4-isobutylresorcinol (patent literature 4). For example, it can be produced by the following method.

With 1,3-dihydroxybenzene, a saturated carboxylic acid or a saturated carboxylic acid halide is reacted in the presence of a Lewis acid such as zinc chloride or aluminum chloride by using chloroform, dichloromethane, nitromethane, nitrobenzene, chlorobenzene, dichlorobenzene, benzene, toluene, xylene, etc. as the solvent (Friedel-Crafts reaction). Then, 4-isobutylresorcinol can be obtained by the reduction with zinc amalgam/hydrochloric acid.

Examples of 4-alkylresorcinol derivatives include phosphoric acid ester derivatives, in which one or more hydrogen atoms of phenolic hydroxyl groups of the 4-alkylresorcinol are substituted with —P(O)(OR$_1$)(OR$_2$). Here, R$_1$ and R$_2$ represent linear or branched alkyl groups of 2 to 5 carbon atoms or hydrogen atoms, and R$_1$ and R$_2$ are the same or different from each other (patent literature 5).

As the salt of the above-described alkoxysalicylic acid, 4-alkylresorcinol, and 4-alkylresorcinol derivatives, alkali metal salts (Na salt, K salt, etc.), alkaline earth metal salts (Ca salt, Mg salt, etc.), ammonium salts, alkanolamine salts, amino acid salts, etc. can be listed, and the alkali metal salts are preferable.

Other than those described above, for example, ascorbic acid or a derivative thereof, specifically sodium L-ascorbate, L-ascorbic acid ester magnesium salt, L-ascorbic acid glucoside, 2-O-ethyl-L-ascorbic acid, or 3-O-ethyl-L-ascorbic acid; tranexamic acid, arbutin, or 4-methoxysalicylic acid salts, specifically 4-methoxysalicylic acid sodium salt, 4-methoxysalicylic acid potassium salt, etc. can be blended.

Various extracts (for example, chestnut rose, yarrow, melilot, phellodendron bark, coptis rhizome, lithospermum root, peony, swertia japonica, birch, sage, loquat, carrot, aloe, mallow, iris, grape, coix seed, luffa, lily, saffron, cnidium root, ginger, hypericum, Ononis spinosa, garlic, pepper, citrus unshiu peel, Angelica acutiloba, seaweed, etc.) may be blended.

In the oil-in-water emulsion composition of the present invention, to promote the absorption of the above-described medicinal components, absorption enhancers that are normally used for cosmetics and external skin preparations may be blended. Such examples include lauryl betaine (product name: Anon BL-SF, manufactured by NOF Corporation), isostearic acid (product name: Isostearic acid EX, manufactured by Kokyu Alcohol Kogyo Co., Ltd.), etc.

In the oil-in-water emulsion composition of the present invention, in addition to the above components, UV absorbers, metal ion sequestering agents, powder components, pH adjusters, vitamins, antioxidants, preservatives, antimicrobial agents, neutralizers, perfume, etc., which are normally blended in cosmetics, can be suitably blended as necessary within the range that the effect of the present invention is not impaired. However, they are not limited to these examples.

The oil-in-water emulsion composition of the present invention can take product forms such as lotion, milky lotion, beauty essence, cream, and pre-makeup. Lotion, milky lotion, and beauty essence are especially preferable.

From the standpoint of handling, the viscosity of the oil-in-water emulsion composition of the present invention, measured at 30 deg C. with a B-type rotating viscometer, is preferably in the range of 1000 to 6000 milli-Pascal second (mPa·s).

The oil-in-water emulsion composition of the present invention can be prepared according to the conventional method. For example, the oil phase obtained by mixing and heating oil-soluble components (including component (c)) is gradually added to the water phase obtained by mixing and heating water-soluble components (including components (a), (b), (d), and (e)) while the water phase is stirred/mixed, resulting in a uniform state of the mixture. Subsequently, the preparation can be completed by cooling the mixture to room temperature.

Example 1

The present invention is further described in the following Examples, however, the invention is not limited by these examples. Unless otherwise specified, the blending amount is indicated by % by mass.

Cosmetics described in Tables 1 to 4 were prepared according to a conventional method. Professional panelists carried out an actual use test to evaluate the items (1) to (8) described below.

<Evaluation Items (1) to (7)>

Ten professional panelists applied each cosmetic to their face twice daily in the morning and evening for 28 days. After the 28 days application, they evaluated (1) an improving effect on wrinkles, (2) an improving effect on elasticity, (3) a spreadability of the cosmetic during application, (4) an absence of oily feeling, (5) a skin smoothing effect, (6) an absence of sticky feeling, and (7) a skin moisturizing effect. The results were shown in the tables according to the criteria mentioned below.

◎: All ten panelists answered that the cosmetic produced said effect or said feeling.

○: Seven to nine panelists answered that the cosmetic produced said effect or said feeling.

Δ: Three to six panelists answered that the cosmetic produced said effect or said feeling.

x: Two or less panelists answered that the cosmetic produced said effect or said feeling.

<Evaluation Item (8); Whitening Effect>

Panelists received sunlight for 2 hours per day for 2 days, totally 4 hours in summer. Then, they applied one of the cosmetics selected from the Examples and Comparative Examples, on a half side of their face, twice daily in the morning and evening for 6 weeks. After the application for 6 weeks, they evaluated an inhibitory effect of the cosmetic they applied on an UV-induced pigmentation, by comparing the degree of pigmentation between both sides of their face. The evaluation for each cosmetic was done with 10 panelists. The results were shown in the tables according to the criteria mentioned below.

◎: All ten panelists answered that the cosmetic had the inhibitory effect.

○: Seven to nine panelists answered that the cosmetic had the inhibitory effect.

Δ: Three to six panelists answered that the cosmetic had the inhibitory effect.

x: Two or less panelists answered that the cosmetic had the inhibitory effect.

Regarding a viscosity of the compositions, the composition was kept at 30 deg C., and then its viscosity (mPa·s) was measured with a B-type rotating viscometer (Vismetron Viscometer, manufactured by Shibaura Systems Co., Ltd.) after rotating at 12 rpm for 1 min.

The following products were used as a component marked with an asterisk (*) in Table 1 to 4.

*1: Softisan 649 (manufactured by Sasol Ltd.)
*2: RA-G-308 (manufactured by Nippon Fine Chemical Co., Ltd.)
*3: Silicone KF-96A-6cs (manufactured by Shin-Etus Chemical Co., Ltd.)
*4: Pemulen TR-2 (manufactured by BF Goodrich Co.)
*5: Biohyalo 9 (manufactured by Shiseido Co., Ltd.)
*6: Aristoflex HMB (manufactured by Clariant (Japan) K.K)
*7: Aristoflex AVC (manufactured by Clariant (Japan) K.K.)
*8: POE(14)/POP(7) dimethyl ether (random)
*9: Anon BL-SF, manufactured by NOF Corporation.
*10: Isostearic acid EX, manufactured by Kokyu Alcohol Kogyo Co., Ltd.

Test 1: Effects of Blending the Components (a) to (e) of the Prevent Invention.

Cosmetics shown in Tables 1 were prepared according to a conventional method and evaluated for the items in the table.

TABLE 1

| | | | Examples | | Comparative examples | | | | | | |
|---|---|---|---|---|---|---|---|---|---|---|---|
| | | Formulation | 1 | 2 | 1 | 2 | 3 | 4 | 5 | 6 | 7 |
| Oil-soluble components | c | Water-holding oil*1 | 2.0 | 0.5 | 2.0 | 2.0 | — | — | — | 0.5 | 0.5 |
| | | Deodorized polybutene | — | — | — | — | — | 2.0 | — | — | — |
| | | Glyceryl tri-2-ethylhexanoate*2 | — | 1.0 | — | 1.0 | 1.0 | 1.0 | — | 1.0 | 1.0 |
| | | Methyl polysiloxane*3 | 2.0 | 3.0 | 2.0 | 3.0 | 3.0 | 3.0 | — | 3.0 | 3.0 |
| | | Olefin oligomer | 2.0 | — | 2.0 | — | — | — | 3.0 | — | — |
| Emulsifiers | | Acrylates/alkyl methacrylate copolymers*4 | 0.07 | 0.05 | 0.07 | 0.07 | 0.05 | 0.05 | 0.07 | 0.05 | 0.05 |
| Thickeners | a | Sodium hyaluronate*5 | 0.3 | 0.5 | — | 0.3 | 0.5 | 0.5 | — | 0.5 | 0.5 |
| | b | Ammonium acryoyldimethyltaurate/beheneth-25 methacrylate crosspolymer*6 | 0.4 | 0.3 | 0.7 | — | 0.3 | 0.3 | 0.4 | 0.3 | 0.3 |
| | | Ammonium acryoyldimethyltaurate/VP copolymer*7 | — | 0.1 | — | 0.4 | 0.1 | 0.1 | — | 0.1 | 0.1 |
| Moisturizers | d | Glycerin | 5.0 | 8.0 | 5.0 | 5.0 | 8.0 | 8.0 | 5.0 | — | 8.0 |
| | | 1,3-butylene glycol | — | 1.0 | — | 3.0 | 1.0 | — | 1.0 | 1.0 | 1.0 |
| | | Dipropylene glycol | — | 1.0 | — | — | 1.0 | 1.0 | — | 1.0 | 1.0 |

TABLE 1-continued

|  |  | Formulation | Examples | | Comparative examples | | | | | | |
|---|---|---|---|---|---|---|---|---|---|---|---|
|  |  |  | 1 | 2 | 1 | 2 | 3 | 4 | 5 | 6 | 7 |
| e<br>Water-soluble<br>components |  | Polyethylene glycol (MMW 4000) | 4.0 | — | 4.0 | 4.0 | — | — | 4.0 | — | — |
|  |  | Polyethylene glycol (MMW 300) | 4.0 | — | 4.0 | 4.0 | — | — | 4.0 | — | — |
|  |  | Ethanol | 7.0 | 5.0 | 7.0 | 7.0 | 5.0 | 5.0 | 7.0 | 5.0 | — |
|  |  | Potassium hydroxide | 0.05 | 0.03 | 0.05 | 0.04 | 0.03 | 0.03 | 0.04 | 0.03 | 0.03 |
|  |  | Edetate | 0.01 | 0.01 | 0.01 | 0.01 | 0.01 | 0.01 | 0.01 | 0.01 | 0.01 |
|  |  | Sodium pyrosulfite | 0.03 | 0.03 | 0.03 | 0.03 | 0.03 | 0.03 | 0.03 | 0.03 | 0.03 |
|  |  | Citric acid | 0.02 | 0.02 | 0.02 | 0.02 | 0.02 | 0.02 | 0.02 | 0.02 | 0.02 |
|  |  | Sodium citrate | 0.08 | 0.08 | 0.08 | 0.08 | 0.08 | 0.08 | 0.08 | 0.08 | 0.08 |
|  |  | Phenoxyethanol | 0.5 | 0.5 | 0.5 | 0.5 | 0.5 | 0.5 | 0.5 | 0.5 | 0.5 |
|  |  | Purified water | Balance | Balance | Balance | Balance | Balance | Balance | Balance | Balance | Balance |
|  |  | Evaluation |  |  |  |  |  |  |  |  |  |
|  |  | (1) Wrinkle improving effect | ◉ | ◉ | Δ | ○ | Δ | Δ | X | ◉ | ◉ |
|  |  | (2) Elasticity improving effect | ◉ | ◉ | Δ | ◉ | X | Δ | X | ◉ | ◉ |
|  |  | (3) Spreadability during application | ◉ | ◉ | ○ | ○ | ○ | ○ | ◉ | Δ | Δ |
|  |  | (4) Absence of oily feeling | ◉ | ◉ | ○ | Δ | Δ | Δ | Δ | X | ○ |
|  |  | (5) Skin smoothing effect after application | ◉ | ◉ | Δ | X | Δ | Δ | Δ | Δ | ◉ |
|  |  | (6) Absence of sticky feeling | ◉ | ◉ | ◉ | ○ | ◉ | ◉ | ○ | X | X |
|  |  | (7) Moist feeling of skin | ◉ | ◉ | Δ | ○ | Δ | ○ | Δ | ◉ | ◉ |

Cosmetics containing all the components (a) to (e) (Examples 1 and 2) generated no oily feeling and sticky feeling, the spreadability during application was good, and it was excellent in the effect to make the skin moist and smooth after application. In addition, the elasticity improving effect and wrinkle improving effect were excellent.

On the other hand, in the cosmetic that did not contain component (a) sodium hyaluronate (Comparative Example 1), the smoothness of the skin and the moist feeling after application were not satisfactory, and the elasticity improving effect and wrinkle improving effect were poor. In the cosmetic in which component (b) ammonium acryloyldimethyltaurate/beheneth-25 methacrylate crosspolymer was replaced with a copolymer of ammonium acryloyldimethyltaurate and vinylpyrrolidone (VP) (Comparative Example 2), the smoothness of the skin after application could not be obtained, and an oily feeling was present. In the cosmetic that did not contain (c) water-holding oil (Comparative Example 3) or the cosmetic in which component (c) was replaced with non-water-holding oil (Comparative Example 4), the smoothness of the skin was poor, an oily feeling was present, the moist feeling tended to be impaired, and the elasticity improving effect and wrinkle improving effect were poor. In the cosmetic that did not contain both components (a) and (c) (Comparative Example 5), the smoothness of the skin and the moist feeling after application were poor, an oily feeling was recognized, and the elasticity improving effect and wrinkle improving effect could not be obtained.

Accordingly, component (b) ammonium acryloyldimethyltaurate/beheneth-25 methacrylate crosspolymer of the present invention was shown to have an excellent effect to make the skin smooth after application. It was also shown that the co-blending of component (a) hyaluronic acid or a salt thereof and (c) water-holding oil provides a moist feeling and smoothness to the skin and generates an excellent improving effect on elasticity and wrinkle.

In the cosmetic that did not contain component (d) glycerin (Comparative Example 6), the sticky feeling and oily feeling were strong, and the spreadability during application and the smoothness after application were also poor. In the cosmetic that did not contain component (e) ethanol (Comparative Example 7), the sticky feeling was strong, and the spreadability during application was poor.

From these results, it was clarified that an oil-in-water emulsion composition without an oily feeling and sticky feeling, good in spreadability during application, excellent in the effect to make the skin moist and smooth after application, and high in the elasticity improving effect and wrinkle improving effect can be prepared by blending components (a) to (e) of the present invention.

Test 2: Preferable Blending Quantities of the Components (a) to (e).

In order to examine a suitable amount of the component (a) to (e) in the compositions, cosmetics shown in Tables 2 were prepared and evaluated for the items (1) to (7).

TABLE 2

|  |  | Formulation | Examples | | | | | | | | | |
|---|---|---|---|---|---|---|---|---|---|---|---|---|
|  |  |  | 3 | 4 | 5 | 6 | 7 | 8 | 9 | 10 | 11 | 12 |
| Oil-soluble<br>components | c | Water-holding oil*1 | 2.0 | 2.0 | 2.0 | 2.0 | 0.5 | 3.0 | 2.0 | 2.0 | 2.0 | 2.0 |
|  |  | Methyl polysiloxane*2 | 2.0 | 2.0 | 2.0 | 2.0 | 2.0 | 2.0 | 2.0 | 2.0 | 2.0 | 2.0 |
|  |  | Olefin oligomer | 2.0 | 2.0 | 2.0 | 2.0 | 2.0 | 2.0 | 2.0 | 2.0 | 2.0 | 2.0 |
| Emulsifiers |  | Acrylates/alkyl methacrylates-copolymers*4 | 0.07 | 0.07 | 0.07 | 0.07 | 0.07 | 0.07 | 0.07 | 0.07 | 0.07 | 0.07 |
| Thickeners | a | Sodium hyaluronate*5 | 0.1 | 0.7 | 0.3 | 0.3 | 0.3 | 0.3 | 0.3 | 0.3 | 0.3 | 0.3 |
|  | b | Ammonium acryoyldimethyltaurate/Beheneth-25 methacrylate crosspolymer*6 | 0.4 | 0.4 | 0.1 | 1.0 | 0.4 | 0.4 | 0.4 | 0.4 | 0.4 | 0.4 |

TABLE 2-continued

|  | Formulation | Examples | | | | | | | | | |
|---|---|---|---|---|---|---|---|---|---|---|---|
|  |  | 3 | 4 | 5 | 6 | 7 | 8 | 9 | 10 | 11 | 12 |
| Moisturizers d | Glycerin | 5.0 | 5.0 | 5.0 | 5.0 | 5.0 | 5.0 | 3.0 | 10.0 | 5.0 | 5.0 |
|  | Polyethylene glycol (MMW 4000) | 4.0 | 4.0 | 4.0 | 4.0 | 4.0 | 4.0 | 4.0 | 4.0 | 4.0 | 4.0 |
|  | Polyethylene glycol (MMW 300) | 4.0 | 4.0 | 4.0 | 4.0 | 4.0 | 4.0 | 4.0 | 4.0 | 4.0 | 4.0 |
| e | Ethanol | 7.0 | 7.0 | 7.0 | 7.0 | 7.0 | 7.0 | 7.0 | 7.0 | 3.0 | 10.0 |
| Water-soluble | Potassium hydroxide | 0.05 | 0.05 | 0.05 | 0.05 | 0.05 | 0.05 | 0.05 | 0.05 | 0.05 | 0.05 |
| components | Edetate | 0.03 | 0.03 | 0.03 | 0.03 | 0.03 | 0.03 | 0.03 | 0.03 | 0.03 | 0.03 |
|  | Sodium pyrosulfite | 0.03 | 0.03 | 0.03 | 0.03 | 0.03 | 0.03 | 0.03 | 0.03 | 0.03 | 0.03 |
|  | Citric acid | 0.02 | 0.02 | 0.02 | 0.02 | 0.02 | 0.02 | 0.02 | 0.02 | 0.02 | 0.02 |
|  | Sodium citrate | 0.08 | 0.08 | 0.08 | 0.08 | 0.08 | 0.08 | 0.08 | 0.08 | 0.08 | 0.08 |
|  | Phenoxyethanol | 0.5 | 0.5 | 0.5 | 0.5 | 0.5 | 0.5 | 0.5 | 0.5 | 0.5 | 0.5 |
|  | Purified water | Balance | Balance | Balance | Balance | Balance | Balance | Balance | Balance | Balance | Balance |
|  | Evaluation |  |  |  |  |  |  |  |  |  |  |
| Viscosity (mPa · s at 30° C.) |  | 2050 | 3100 | 1400 | 6700 | 2300 | 3400 | 2700 | 4800 | 3800 | 2600 |
| (1) Wrinkle improving effect |  | ○ | ○ | ○ | ○ | ○ | ○ | ○ | ◎ | ◎ | ◎ |
| (2) Elasticity improving effect |  | ◎ | ◎ | ◎ | ◎ | ○ | ◎ | ◎ | ○ | ◎ | ◎ |
| (3) Spreadability during application |  | ◎ | ◎ | ◎ | ◎ | ◎ | ○ | ◎ | ○ | ○ | ○ |
| (4) Absence of oily feeling |  | ◎ | ◎ | ◎ | ◎ | ◎ | ◎ | ◎ | ○ | ○ | ○ |
| (5) Smoothness of skin after application |  | ◎ | ◎ | ◎ | ◎ | ◎ | ◎ | ◎ | ○ | ◎ | ◎ |
| (6) Absence of sticky feeling |  | ◎ | ◎ | ◎ | ◎ | ◎ | ◎ | ◎ | ○ | ○ | ◎ |
| (7) Moist feeling of skin |  | ○ | ◎ | ◎ | ◎ | ○ | ○ | ○ | ◎ | ◎ | ◎ |

The results in Table 2 indicates that all the cosmetics containing 0.1 to 0.7 mass % of component (a) (Examples 3 and 4), 0.1 to 1.0 mass % of component (b) (Examples 4 to 6), 0.5 to 3.0 mass % of component (c) (Examples 6 to 8), 3.0 to 10.0 mass % of component (d) (Examples 8 to 10), and 3.0 to 10.0 mass % of component (e) (Examples 10 to 12) did not have an oily feeling and sticky feeling, the spreadability during application was good, the effect to make the skin moist and smooth after application was excellent, and the elasticity improvement effect and wrinkle improvement effect were also excellent.

Thus, it was found that the preferable blending quantities of components (a) to (e) of the present invention are as follows: component (a) is 0.3 to 0.7 mass %, component (b) is 0.3 to 0.7 mass %, component (c) is 1.0 to 2.0 mass %, component (d) is 4.0 to 8.0 mass %, and component (e) is 5.0 to 8.0 mass %.

Test 3: Whitening Effect Due to a Further Blending of Whitening Agents.

In addition to the components (a) to (e), whitening agents were further blended into the composition of the present invention, and the whitening effect was evaluated.

TABLE 3

|  | Formulation | Examples | | | |
|---|---|---|---|---|---|
|  |  | 13 | 14 | 15 | 16 |
| Oil-soluble c | Water-holding oil[*1] | 2.0 | 0.5 | 2.0 | 2.0 |
| components | Glyceryl tri-2-ethylhexanoate[*2] | — | 1.0 | — | — |
|  | Methyl polysiloxane[*3] | 2.0 | 3.0 | 2.0 | 2.0 |
|  | Olefin oligomer | — | — | 2.0 | 2.0 |
|  | POE(14)/POP(7) dimethyl ether[*8] | — | 0.1 | — | — |
| Emulsifiers | Acrylates/alkyl methacrylate copolymers[*4] | 0.07 | 0.05 | 0.07 | 0.07 |
| Thickeners a | Sodium hyaluronate[*5] | 0.3 | 0.5 | 0.3 | 0.3 |
| b | Ammonium acryoyldimethyltaurate/beheneth-25 methacrylate crosspolymer[*6] | 0.4 | 0.3 | 0.5 | 0.6 |
|  | Ammonium acryoyldimethyltaurate/VP copolymer[*7] | — | 0.1 | — | — |
| Moisturizers d | Glycerin | 5.0 | 5.0 | 5.0 | 5.0 |
|  | 1,3-butylene glycol | — | 1.0 | — | — |
|  | Dipropylene glycol | — | 1.0 | — | — |
|  | Polyethylene glycol (MMW 4000) | 4.0 | — | 4.0 | 4.0 |
|  | Polyethylene glycol (MMW 300) | 4.0 | — | 4.0 | 4.0 |
| e | Ethanol | 7.0 | 7.0 | 7.0 | 7.0 |
| Whitening | 4-isobutylresorcinol | — | 0.25 | — | 0.25 |
| agents | potassium 4-methoxysalicylate | — | — | 1.0 | 1.0 |
| Water-soluble | Potassium hydroxide | 0.05 | 0.03 | 0.05 | 0.05 |
| components | Edetate | 0.03 | 0.01 | 0.01 | 0.01 |
|  | Sodium pyrosulfite | — | 0.03 | 0.03 | 0.03 |
|  | Citric acid | 0.02 | 0.02 | 0.02 | 0.02 |
|  | Sodium citrate | 0.08 | 0.08 | 0.08 | 0.08 |
|  | Phenoxyethanol | 0.5 | 0.5 | 0.5 | 0.5 |
|  | Purified water | Balance | Balance | Balance | Balance |
|  | Evaluation |  |  |  |  |
| Viscosity (mPa · s at 30° C.) |  | 3500 | 3000 | 2300 | 4000 |
| (1) Wrinkle improving effect |  | ◎ | ◎ | ◎ | ◎ |
| (2) Elasticity improving effect |  | ◎ | ◎ | ◎ | ◎ |

TABLE 3-continued

| Formulation | Examples | | | |
|---|---|---|---|---|
| | 13 | 14 | 15 | 16 |
| (3) Spreadability during application | ◎ | ◎ | ◎ | ◎ |
| (4) Absence of oily feeling | ◎ | ◎ | ◎ | ◎ |
| (5) Smoothness of skin after application | ◎ | ◎ | ◎ | ◎ |
| (6) Absence of sticky feeling | ◎ | ◎ | ◎ | ◎ |
| (7) Moist feeling of skin | ◎ | ◎ | ◎ | ◎ |
| (8) Whitening effect | Δ | ○ | ○ | ◎ |

The cosmetics in which 4-isobutylresorcinol (Example 14) or potassium 4-methoxysalicylate (Example 15) was blended as the whitening agent were excellent in the whitening effect compared with the cosmetic which did not contain any whitening agent (Example 13). The cosmetic in which both 4-isobutylresorcinol and potassium 4-methoxysalicylate were blended (Example 16) was far superior in the whitening effect to the cosmetic which contained one of those whitening agents. All the cosmetics of Examples 14 to 16 were without an oily feeling and sticky feeling, good in the spreadability during application, excellent in the effect to make the skin moist and smooth after application, and also excellent in the elasticity improvement effect and wrinkle improvement.

Accordingly, it was clarified that, by the addition of a whitening agent in addition to the components (a) to (e) of the present invention, an oil-in-water emulsion composition without an oily feeling and sticky feeling, good in a spreadability during application, excellent in the effect to make the skin moist and smooth after application, excellent in the effect on elasticity improvement and wrinkle improvement, and also excellent in the whitening effect can be prepared.

Test 4: Effect on Water Content in the Stratum Corneum.

As described, a formation of fine wrinkles is thought to be correlated with water content in the stratum corneum. Therefore, in order to understand the excellent wrinkle improving effect of the compositions of the present invention, an influence of the present compositions on water content in the stratum corneum was examined.

Cosmetic shown in Tables 4 was prepared and confirmed to have no oily feeling and sticky feeling, a good spreadability during application, an excellent moisturizing and smoothing effects for the skin, and an excellent wrinkle improving and elasticity improving effect.

TABLE 4

| Formulation | | | Example 17 |
|---|---|---|---|
| Oil-soluble components | c | Water-holding oil *[1] | 1.0 |
| | | Glyceryl tri-2-ethylhexanoate *[2] | 2.0 |
| | | Methyl polysiloxane *[3] | 1.0 |
| | | Olefin oligomer | 1.0 |
| | | POE(14)/POP(7) dimethyl ether *[8] | 0.1 |
| Emulsifiers | | Acrylates/alkyl methacrylate copolymer *[4] | 0.05 |
| Thickeners | a | Sodium hyaluronate *[5] | 0.5 |
| | b | Ammonium acryoyldimethyltsurate/beheneth-25 methacrylate crosspolymer *[6] | 0.3 |
| | | Ammonium acryoyldimethyltsurate/VP copolymer *[7] | 0.1 |
| Moisturizers | d | Glycerin | 3.0 |
| | | 1,3-butylene glycol | 1.0 |
| | | Dipropylene glycol | 1.0 |
| | | Polyethylene glycol (MMW 4000) | 2.0 |
| | | Polyethylene glycol (MMW 300) | 2.0 |
| | e | Ethanol | 5.0 |
| Absorption enhancene | | Lauryl betaine *[9] | 0.04 |
| | | Isostearic acid *[10] | 0.06 |
| Perfume | | Perfume | 0.10 |

TABLE 4-continued

| Formulation | | Example 17 |
|---|---|---|
| Water-soluble components | Potassium hydroxide | 0.05 |
| | Edetate | 0.01 |
| | Sodium pyrosulfite | 0.003 |
| | Citric acid | 0.03 |
| | Sodium citrate | 0.07 |
| | Phenoxyethanol | 0.5 |
| | Purified water | Balance |
| Evaluation | | |
| Viscosity (mPa · s at 30° C.) | | 3100 |
| (1) Wrinkle improving effect | | ◎ |
| (2) Elasticity improving effect | | ◎ |
| (3) Spreadability during application | | ◎ |
| (4) Absence of oily feeling | | ◎ |
| (5) Smoothness of skin after application | | ◎ |
| (6) Absence of sticky feeling | | ◎ |
| (7) Moist feeling of skin | | ◎ |

An influence of the cosmetic of Example 17 on water content in the stratum corneum was examined by in-vivo measurement using the Corneometer (Corneometer,™). Corneometry using the Corneometer is a technique to non-invasively determine water content in the stratum corneum. The details are described below.

<Measuring Procedure>

Twenty healthy women aged between 44 and 61 years old (Mean age: 54 years old) presenting a dry skin on their forearms were used as subjects. One of their forearms was selected as a treated forearm to receive a composition, and the other one was used as a non-treated forearm not to receive any composition. The following 4 areas were marked on the inner of the forearms.

$C_1$: one control area (2×2 cm$^2$) on the non-treated forearm $Z_{1-3}$: three treated areas (2×4 cm$^2$ for each area) on the treated forearm (Treatment on a Treated Forearm)

In order to adjust an environmental condition, the subjects had been in a room under controlled temperature at 21+/−1 deg C. and relative humidity of 45+/−5% for 20 minutes. After the rest period, measurements with the Corneometer (Corneometer CM825, manufactured by Courage and Khazaka Electronic, Germany) were carried out on $C_1$ and on either $Z_1$, $Z_2$, or $Z_3$ area to obtain a capacitance before the application (=$T_0$) at each $Z_{1-3}$ area. Then, 16 microliter of the composition of the present invention was applied on each $Z_{1-3}$ area.

The subjects kept being in the room under the same environmental condition. The capacitances at 30 minutes (=$T_{0.5}$), 4 hours (=$T_4$), and 8 hours (=$T_8$) after the application were measured in the same way as described above. Three measurements were performed on each treated area for each subject and each examination time, and the mean of the 3 measurements was calculated.

(Treatment on a Non-Treated Forearm)

The same treatment as that on a treated forearm, except for the application of the composition of the present invention, was performed on a non-treated forearm, and the values of $T_{0.5}$, $T_4$, and $T_8$ were measured.

<Evaluation of Water Content in the Stratum Corneum>

The capacitance obtained by corneometry is positively correlated with water content in the stratum corneum. Thus, the capacitance after the application (=$T_{0.5}$, $T_4$, and $T_8$) was expressed as a value relative to that before the application (=$T_0$), to evaluate the effect of the present composition on water content in the stratum corneum.

<Results>

The results obtained by the procedure described above were shown in Table 5. The water content in the stratum corneum on (1) treated forearms statistically differs from that on (2) non-treated forearms at each examination time, at 5% level of significance.

TABLE 5

|  | Example 17 | | |
|---|---|---|---|
| Water content in stratum corneum (%) | 0.5 hr | 4 hr | 8 hr |
| (1) Treated forearm | 150.5% | 143.2% | 136.8% |
| (2) Non-treated forearm | 105.3% | 108.8% | 106.3% |
| (3) Moisturizing Effect of the composition (=(1) − (2)) | 145.2% | 134.3% | 130.4% |

In Table 5, the value obtained by subtracting the water content in the stratum corneum on (1) treated forearm from the content on (2) non-treated forearm (=(3)) represents an increase in water content in the stratum corneum, i.e., a moisturizing effect produced by the composition of the present invention. Thus, the water content in the stratum corneum was shown to increase by 45.2% at 30 minutes, by 34.3% at 4 hours, and by 30.4% even at 8 hours after the application of the cosmetic of Example 17, compared with the water content before the application.

Accordingly, it was clarified that the oil-in-water emulsion composition of the present invention has a very high moisturizing effect, and its single application leads to a prolonged increase of water retention capacity of the skin.

Test 5: Inhibitory Effect on Desquamation.

Desquamation, a shedding of corneocytes from the skin surface, is a physiological phenomenon correlated with water content in the stratum corneum. An increase in water content in the stratum corneum is known to lead to a decrease in desquamation. Thus, an influence of the composition of the present invention on desquamation was examined.

<Measuring Procedure>

Thirty-two female subjects applied the cosmetic of Example 17 on one of their legs (=treated legs) twice daily in the morning and evening for 28 days.

(Treatment on a Treated Leg)

In order to adjust an environmental condition, the subjects had been in a room under controlled temperature at 21+/−1 deg C. and relative humidity of 45+/−5% for 20 minutes. After the rest period, D-Squames™, which were clear adhesives, were pasted on the treated leg for 5 to 20 seconds and then carefully peeled from the leg. The peeled D-Squames were placed on a glass slide, and the glass slide with the peeled D-Squames was then positioned on a smooth black support. Digital images of the peeled D-Squames were obtained by the use of optical equipment. The intensity of grey pixel (hereinafter referred to as grey level) on the image is correlated with the number of corneocytes peeled with the D-Squames. Thus, in the present invention, a gray level in an arbitrary area of 1.4 cm² on the image was quantified and used as an index which represents a level of desquamation (=$T_{28}$).

(Treatment on a Non-Treated Leg)

The same treatment as that on a treated leg was performed on a non-treated leg, and an index of desquamation on a non-treat leg (=$T_0$) was obtained.

<Evaluation of an Inhibitory Effect of the Composition on Desquamation>

In order to evaluate an inhibitory effect of the composition of the present invention, rate of decrease in the index of desquamation on a treated leg (=$T_{28}$) compared with that on a non-treated leg (=$T_0$) was calculated according to the following formula;

Rate of decrease in desquamation (%)=[($T_{28}$−$T_0$)/$T_0$]×100

<Results>

The results obtained by the procedure described above (means+/−standard deviations) were shown in Table 6. The value of $T_{28}$ statistically differs from the value of $T_0$ at 5% level of significance.

TABLE 6

| Level of desquamation | | Example 17 |
|---|---|---|
| Index of desquamation on non-treated leg (=$T_0$) | | 48.31 ± 4.67 |
| Index of desquamation on treated leg (=$T_{28}$) | | 44.28 ± 5.49 |
| Inhibitory effect of the composition on desquamation | Decrease in desquamation (=$T_{28}$ − $T_0$) | −4.03 ± 6.84 |
| | Rate of decrease in desquamation (%) (=[($T_{28}$ − $T_0$)/$T_0$] × 100) | −8.3% |

The index of desquamation on the treated leg decreased by 8.3% compared with that on the non-treated leg. These data indicate that an application of the composition of the present invention significantly inhibits desquamation, i.e., a shedding of corneocytes from skin surface.

Accordingly, it was clarified that a continuous application of the composition of the present invention results in a prolonged enhancement of the water retention capability of the stratum corneum, leading to an inhibition of the shedding of corneocytes.

Test 6: Effect on Skin Viscoelasticity.

Next, in order to understand the excellent elasticity improving effect of the compositions of the present, an influence of the present compositions on skin viscoelasticity was examined using the Cutometer™. Cutometry using the Cutometer is a technique to evaluate skin viscoelasticity by measuring an elastic recovery rate of the skin. In the measurement using the Cutometer, a sensor is put on the surface of the skin to measure the elastic recovery after suctioning/releasing.

<Measuring Procedure>

Thirty-three healthy women aged between 45 and 67 years old were used as subjects, and one of their temples (right or left temple) was randomly selected as a measurement site. According to the method described below, viscoelasticity at the site was measured before application ($T_0$) and after application of the cosmetic of Example 17 for 28 days ($T_{28}$). The cosmetic was applied twice daily in the morning and evening for the period.

Environmental conditions were adjusted by making the subjects stay in a room under controlled temperature at 21+/−1 deg C. and relative humidity of 45+/−5% for 20 minutes. Then, the measurements were carried out with the Cutometer (Cutometer SEM575, manufactured by Courage and Khazaka Electronic, Germany) under the conditions of 300 mbar-negative pressure and 2 mm-diameter of probe. Three measurements were performed on each measurement site for each examination time ($T_0$ and $T_{28}$,), and the mean and standard deviation were calculated.

<Evaluation of the Skin Viscoelasticity>

The measurement with the Cutometer leads to a determination of the following parameters shown in FIG. 2. Among those parameters, an elastic recovery rate (Ur/Uf) is given as the value of an immediate elastic recovery (Ur, expressed in mm) divided by the value of a maximum extensibility (Uf, expressed in mm). The higher the elastic recovery rate, the higher the skin viscoelasticity.

<Results>

The results obtained by the procedure described above were shown in Table 7 (means+/−standard deviations). For all parameters shown in Table 7, the value obtained at 28 days after the application ($T_{28}$) statistically differed from the value obtained before application ($T_0$) at 5% level of significance.

TABLE 7

| Studied parameters | Example 17 | |
| --- | --- | --- |
|  | Before application (=$T_0$) | After 28 days application (=$T_{28}$) |
| Ur: Immediate elastic recovery (mm) | 0.057 ± 0.012 | 0.065 ± 0.011 |
| Uf: Maximum extensibility (mm) | 0.294 ± 0.050 | 0.302 ± 0.050 |
| Ur/Uf: Elastic recovery rate (Relative value) | 0.197 ± 0.041 (100.0%) | 0.217 ± 0.042 (110.4%) |

As shown in Table 5, there was a significant difference both in the immediate elastic recovery (Ur) and the maximum extensibility (Uf) between the skin before application ($T_0$) and the skin after 28 days application ($T_{28}$). The elastic recovery rate (Ur/Uf) increased by 10.4% on the skin after the application (110.4%) compared with the skin before application (100.0%).

Accordingly, it was clarified that the composition of the present invention is capable of increasing a skin viscoelasticity to a great extent, thereby leading to an improvement of elastic feeling.

Test 7: Other Effects on the Skin and Feelings in Use.

In addition to the effects on the skin (the moisturizing effect, skin smoothing effect, and improving effect on wrinkles and elasticity) and the feelings of the composition in use (the good spreadability during application, no oily feeling, and no sticky feeling) described above, the composition of the present invention was found to produce a variety of favorable effects on the skin and feelings in use. A part of them is shown below.

Thirty-three female subjects applied the cosmetic of Example 17 on their whole face twice daily in the morning and evening for 28 days, and then evaluated the following 13 items according to the criteria bellow.

A: Totally agree
B: Somewhat agree
C: Somewhat disagree
D: Totally disagree

The answers A and B were counted as agree, whereas the answers C and D were counted as disagree. The percentage (%) of the subjects who answered agree among all subjects was calculated, and a statistical evaluation of the percentage was assessed with the Chi-squared test at 5% level of significance.

<Evaluation Items>

Feelings of being effective on the skin;
(1) The skin is softer.
(2) The skin is firmer.
(3) The skin is more elastic.
(4) The skin is restructured.
(5) The skin texture is renewed/given a new life.
(6) The complexion is more even.
(7) The skin is fresher.
(8) The product helps to decrease the skin slackening.
(9) The product has a revitalizing effect.
(10) The skin seems strengthened.

Feelings of the composition in use;
(11) The product penetrates rapidly.
(12) The product texture is pleasant.
(13) The product brings a total comfort.

<Results>

TABLE 8

| Evaluation items | Example 17 | |
| --- | --- | --- |
|  | % Agreement | Significance |
| Feelings of being effective on the skin | | |
| (1) The skin is softer. | 82 | Yes |
| (2) The skin is firmer. | 73 | Yes |
| (3) The skin is more elastic. | 73 | Yes |
| (4) The skin is restructured. | 70 | Yes |
| (5) The skin texture is renewed/given a new life. | 70 | Yes |
| (6) The complexion is more even. | 73 | Yes |
| (7) The skin is fresher. | 79 | Yes |
| (8) The product helps to decrease the skin slackening. | 70 | Yes |
| (9) The product has a revitalizing effect. | 91 | Yes |
| (10) The skin seems strengthened. | 79 | Yes |
| Feelings in use | | |
| (11) The product penetrates rapidly. | 91 | Yes |
| (12) The product texture is pleasant. | 88 | Yes |
| (13) The product brings a total comfort. | 88 | Yes |

As shown in Table 8, 70 to 91% of the subjects agreed that the skin condition was improved as described in the items (1) to (10), and those evaluations were statistically significant. Furthermore, 91 to 88% of the subjects agreed that the composition generated the feelings in use described in the items (11) to (13), and those evaluations were also statistically significant.

Accordingly, it was clarified that, in addition to the effects previously described, the composition of the present invention is effective for making the skin softer and more elastic ((1) to (3)), making the skin texture renewed ((4) to (6)), and revitalizing and strengthening the skin ((7) to (10)). Moreover, the composition of the present invention was found to rapidly penetrate and be good in its texture, resulting in a high level of satisfaction in the feelings in use.

Formulation examples of an oil-in-water emulsion composition of the present invention are shown below, however, the present invention is not limited to them. All the following oil-in-water emulsion compositions are very high in the moisturizing effect and the skin smoothing effect, excellent in the improving effect on wrinkles and elasticity, good in spreadability during application, without an oily feeling and sticky feeling, and excellent in the whitening effect.

Formulation Example 1: Whitening Serum

<Formulation>

| Components | mass % |
|---|---|
| (1) di(phytosteryl/2-octyldodecyl) N-lauroyl-L-glutamate (Eldew PS-203, manufactured by Ajinomoto Co, Inc.) | 1.5 |
| (2) Isodecyl neopentanoate | 3.0 |
| (3) Methyl polysiloxane (1.5 cs) | 1.0 |
| (4) Acrylates/alkyl methacrylate copolymers (*4) | 0.05 |
| (5) Sodium hyaluronate (*5) | 0.3 |
| (6) Ammonium acryloyldimethyltaurate/beheneth-25 methacrylate crosspolymer (*6) | 0.6 |
| (7) Sodium acrylate/sodium acryloyldimethyl taurate copolymer (SIMULGEL EG, manufactured by SEPPIC Ltd.) | 0.1 |
| (8) Glycerin | 6.0 |
| (9) 1,3-butylene glycol | 3.0 |
| (10) Ethanol | 6.0 |
| (11) 4-isobutylresorcinol | 0.25 |
| (12) 4-methoxysalicylic acid potassium salt | 1.0 |
| (13) Perfume | q.s. |
| (14) Potassium hydroxide | q.s. |
| (15) Sodium pyrosulfite | q.s. |
| (16) Ion-exhanged water | balance |

<Production Method>

The oil phase in which the components (1) to (3) were uniformly dispersed was gradually added into the water phase in which the components (4) to (16) were uniformly dispersed. Then, the mixture was emulsified with a homomixer, resulting in production of a whitening serum having a viscosity of 2500 mPa·s at 30 deg C.

Formulation Example 2: General Serum

<Formulation>

| Components | mass % |
|---|---|
| (1) Di(phytosteryl/2-octyldodecyl) N-lauroyl-L-glutamate (Eldew PS-203, manufactured by Ajinomoto Co., Inc.) | 1.5 |
| (2) Isononyl isononanoate | 1.0 |
| (3) Cyclopentasiloxane | 1.0 |
| (4) Acrylates/alkyl methacrylate copolymers (*4) | 0.05 |
| (5) Sodium hyaluronate (*5) | 0.3 |
| (6) Ammonium acryloyldimethyltaurate/beheneth-25 methacrylate crosspolymer (*6) | 0.3 |
| (7) Ammonium polyacrylate (SIMULGEL A, manufactured by SEPPIC Ltd.) | 0.1 |
| (8) Glycerin | 5.0 |
| (9) Dipropylene glycol | 3.0 |
| (10) Ethanol | 6.0 |
| (11) 4-isobutylresorcinol | 0.25 |
| (12) 4-methoxysalicylic acid potassium salt | 1.0 |
| (13) Mother-of-thyme extract | 0.1 |
| (14) Green tea extract | 0.1 |
| (15) Chestnut rose fruit extract | 0.1 |
| (16) Perfume | q.s. |
| (14) Potassium hydroxide | q.s. |
| (15) Sodium pyrosulfite | q.s. |
| (16) Ion-exchanged water | balance |

<Production Method>

The oil phase in which the components (1) to (3) were uniformly dispersed was gradually added into the water phase in which the components (4) to (16) were uniformly dispersed. Then, the mixture was emulsified with a homomixer, resulting in production of a general serum having a viscosity of 2500 mPa·s at 30 deg C.

Formulation Example 3: General Serum

<Formulation>

| Components | mass % |
|---|---|
| (1) Di(phytosteryl/2-octyldodecyl) N-lauroyl-L-glutamate (Eldew PS-203, manufactured by Ajinomoto Co., Inc.) | 1.5 |
| (2) Cetyl ethyhexanoate | 1.0 |
| (3) Methyl polysiloxane | 1.0 |
| (4) Acrylates/alkyl methacrylate copolymers (*4) | 0.05 |
| (5) Sodium hyaluronate (*5) | 0.3 |
| (6) Ammonium acryloyldimethyltaurate/beheneth-25 methacrylate crosspolymer (*6) | 0.3 |
| (7) Sodium acrylate/sodium acryloyldimethyl taurate copolymer (SIMULGEL EG, manufactured by SEPPIC Ltd. | 0.1 |
| (8) Glycerin | 5.0 |
| (9) 1,3-butylene glycol | 3.0 |
| (10) Ethanol | 6.0 |
| (11) 4-isobutylresorcinol | 0.3 |
| (12) 4-methoxysalicylic acid potassium salt | 1.0 |
| (13) Mother-of-thyme extract | 0.1 |
| (14) Yeast extract | 0.1 |
| (15) Water lily extract | 0.1 |
| (16) Perfume | q.s. |
| (17) Potassium hydroxide | q.s. |
| (18) Sodium pyrosulfite | q.s. |
| (19) Ion-exchanged water | balance |

<Production Method>

The oil phase in which the components (1) to (3) were uniformly dispersed was gradually added into the water phase in which the components (4) to (19) were uniformly dispersed. Then, the mixture was emulsified with a homomixer, resulting in production of a general serum having a viscosity of 4400 mPa·s at 30 deg C.

The invention claimed is:

1. An oil-in-water emulsion composition comprising:
    (a) 0.3 to 0.7 mass % of hyaluronic acid or a salt thereof,
    (b) 0.3 to 0.7 mass % of ammonium acryloyldimethyltaurate/beheneth-25 methacrylate crosspolymer,
    (c) 1.0 to 2.0 mass % of an oil with water-holding capacity,
    (d) 5 mass % or less amount of glycerin,
    (e) 5 mass % or more amount of ethanol, and
    (f) 0.01 to 0.1 mass % of acrylates/alkyl methacrylate copolymer, and
    wherein in (c) said oil with water-holding capacity is bis-diglyceryl polyacyladipate-2 or di(phytosteryl/2-octyldodecyl)N-lauroyl-L-glutamate.

2. The oil-in-water emulsion composition according to claim 1, further comprising one or more compound(s) selected from the group consisting of an alkoxysalicylic acid or a salt thereof, a 4-alkylresorcinol or a salt thereof, and a 4-alkylresorcinol derivative or a salt thereof.

3. An A-oil-in-water emulsion cosmetic comprising:
    (a) 0.3 to 0.7 mass % of hyaluronic acid or a salt thereof,
    (b) 0.3 to 0.7 mass % of ammonium acryloyldimethyltaurate/beheneth-25 methacrylate crosspolymer,
    (c) 1.0 to 2.0 mass % of an oil with water-holding capacity,
    (d) 5 mass % or less amount of glycerin,
    (e) 5 mass % or more amount of ethanol, and
    (f) 0.01 to 0.1 mass % of acrylates/alkyl methacrylate copolymer, and
    wherein in (c) said oil with water-holding capacity is bis-diglyceryl polyacyladipate-2 or di(phytosteryl/2-octyldodecyl)N-lauroyl-L-glutamate.

4. The oil-in-water emulsion composition according to claim 1, wherein in (c) said oil with water-holding capacity is bis-diglyceryl polyacyladipate-2.

5. The oil-in-water emulsion composition according to claim 1, wherein in (c) said oil with water-holding capacity is di(phytosteryl/2-octyldodecyl)N-lauroyl-L-glutamate.

6. The oil-in-water emulsion cosmetic according to claim 3, wherein in (c) said oil with water-holding capacity is bis-diglyceryl polyacyladipate-2.

7. The oil-in-water emulsion cosmetic according to claim 3, wherein in (c) said oil with water-holding capacity is di(phytosteryl/2-octyldodecyl)N-lauroyl-L-glutamate.

\* \* \* \* \*

UNITED STATES PATENT AND TRADEMARK OFFICE
CERTIFICATE OF CORRECTION

PATENT NO. : 9,913,788 B2
APPLICATION NO. : 14/650769
DATED : March 13, 2018
INVENTOR(S) : Takayuki Omura et al.

It is certified that error appears in the above-identified patent and that said Letters Patent is hereby corrected as shown below:

In the Claims

Column 20, Line 55, (Claim 3), delete "A-oil-in-water" and insert --oil-in-water--.

Signed and Sealed this
Sixteenth Day of October, 2018

Andrei Iancu
*Director of the United States Patent and Trademark Office*